United States Patent
Sieniek

(10) Patent No.: US 10,936,160 B2
(45) Date of Patent: Mar. 2, 2021

(54) SYSTEM, USER INTERFACE AND METHOD FOR INTERACTIVE NEGATIVE EXPLANATION OF MACHINE-LEARNING LOCALIZATION MODELS IN HEALTH CARE APPLICATIONS

(71) Applicant: Google LLC, Mountain View, CA (US)

(72) Inventor: Marcin Sieniek, Mountain View, CA (US)

(73) Assignee: Google LLC, Mountain View, CA (US)

( * ) Notice: Subject to any disclaimer, the term of this patent is extended or adjusted under 35 U.S.C. 154(b) by 118 days.

(21) Appl. No.: 16/246,156

(22) Filed: Jan. 11, 2019

(65) Prior Publication Data

US 2020/0225811 A1    Jul. 16, 2020

(51) Int. Cl.
*G06F 3/0482* (2013.01)
*G16H 50/30* (2018.01)
(Continued)

(52) U.S. Cl.
CPC ........ *G06F 3/0482* (2013.01); *G06F 3/03543* (2013.01); *G06F 3/04883* (2013.01);
(Continued)

(58) Field of Classification Search
CPC .... G16H 50/30; G16H 50/20; G06F 3/03543; G06F 3/04883; G06N 3/08; G06N 5/04; G06T 7/0012
See application file for complete search history.

(56) References Cited

U.S. PATENT DOCUMENTS

| 9,715,642 B2 | 6/2017 | Szegedy et al. |
| 10,013,781 B1 | 7/2018 | Gammage et al. |

(Continued)

FOREIGN PATENT DOCUMENTS

| WO | 2018/156133 A1 | 8/2018 |
| WO | 2019/022779 A1 | 1/2019 |

OTHER PUBLICATIONS

Lipton, Zachary C., "The Mythos of Model Interpretability", arXiv:1606.03490v3 [cs.LG], Mar. 6, 2017, 9 pages.
(Continued)

*Primary Examiner* — Ruiping Li
(74) *Attorney, Agent, or Firm* — McDonnell Boehnen Hulbert & Berghoff LLP

(57) ABSTRACT

A method and system for assessing a machine learning model providing a prediction as to the disease state of a patient from a 2D or 3D image of the patient or a sample obtained therefrom. The machine learning model produces a prediction of the disease state from the image. The method involves presenting on a display of a workstation the image of the patient or a sample obtained therefrom along with a risk score or classification associated with the prediction. The image is further augmented with highlighting to indicate one or more regions in the image which affected the prediction produced by the machine learning model. Tools are provided by which the user may highlight one or more regions of the image which the user deems to be suspicious for the disease state. Inference is performed on the user-highlighted areas by the machine learning model. The results of the inference are presented to the user via the display.

20 Claims, 7 Drawing Sheets

(51) Int. Cl.
G16H 50/20 (2018.01)
G06F 3/0354 (2013.01)
G06F 3/0488 (2013.01)
G06N 3/08 (2006.01)
G06N 5/04 (2006.01)
G06T 7/00 (2017.01)

(52) U.S. Cl.
CPC ............... *G06N 3/08* (2013.01); *G06N 5/04* (2013.01); *G06T 7/0012* (2013.01); *G16H 50/20* (2018.01); *G16H 50/30* (2018.01); *G06T 2207/30096* (2013.01)

(56) References Cited

U.S. PATENT DOCUMENTS

| | | | | |
|---|---|---|---|---|
| 2012/0053446 | A1* | 3/2012 | Lossev | G06T 7/0012 600/407 |
| 2016/0364862 | A1* | 12/2016 | Reicher | G16H 10/20 |
| 2017/0243085 | A1 | 8/2017 | Vanhoucke et al. | |

OTHER PUBLICATIONS

Weng, Lilian, "How to Explain the Prediction of a Machine Learning Model?", Blog Post, https://lilianweng.github.io/lil-log/2017/08/01/how-to-explain-the-prediction-of-a-machine-learning-model.html, Aug. 1, 2017, pp. 1-7.

Bahdanau, Dzmitry et al., "Neural Machine Translation By Jointly Learning to Align and Translate", Published as a conference paper at ICLR 2015, arXiv:1409.0473v7 [cs.CL], May 19, 2016, pp. 1-15.

Choi, Edward et al., "GRAM: Graph-Based Attention Model for Healthcare Representation Learning", arXiv:1611.07012v3 [cs.LG] Apr. 1, 2017, pp. 1-15.

Choi, Edward et al., "RETAIN: An Interpretable Predictive Model for Healthcare Using Reverse Time Attention Mechanism", 30th Conference on Neural Information Processing Systems (NIPS 2016), Barcelona Spain, arXiv:1608.05745v3 [cs.GL], Feb. 2017, pp. 1-9.

Sundararajan, Mukund et al., "Axiomatic Attribution for Deep Networks", arXiv:1703.01365v2 [cs.LG] Jun. 13, 2017, 11 pages.

Lin, Tsung-Yi, et al. "Focal Loss for Dense Object Detection." Proceedings of the IEEE International Conference on Computer Vision, Aug. 2017, pp. 2980-2988.

Huang, Xiaojie et al., "Lung Nodule Detection in CT Using 3D Convolutional Neural Networks." 2017 IEEE 14th International Symposium on Biomedical Imaging (ISBI 2017). IEEE, Apr. 2017, pp. 379-383.

Ciompi, Francesco, et al. "Towards Automatic Pulmonary Nodule Management in Lung Cancer Screening with Deep Learning." Scientific Reports 7; Apr. 19, 2017, 11 pages.

Sun, Wenqing, et al., "Computer Aided Lung Cancer Diagnosis with Deep Learning Algorithms." Medical Imaging 2016: Computer-Aided Diagnosis, vol. 9785. International Society for Optics and Photonics, 2016, 8 pages.

Chon, Albert, et al. Deep Convolutional Neural Networks for Lung Cancer Detection, Stanford University Reports, 2017, pp. 1-9.

Alakwaa, Wafaa, et al., "Lung Cancer Detection and Classification with 3D Convolutional Neural Network (3D-CNN)." International Journal of Advance Computer Science and Applications, vol. 8, No. 8, 2017, pp. 409-417.

Szegedy, Christian et al., "Going Deeper With Convolutions", arXiv:1409.4842v1 [cs.CV], Sep. 17, 2014, pp. 1-12.

Szegedy, Christian et al., "Rethinking the Inception Architecture for Computer Vision", arXiv:1512.00567v3 [cs.CV], Dec. 11, 2015, 10 pages.

Szegedy, Christian et al., "Inception-v4, Inception-ResNet and the Impact of Residual Connections on Learning", Proceedings of the Thirty-First AAAI Conference on Artificial Intelligence (AAAI-17), vol. 4, 2017, pp. 4278-4284.

* cited by examiner

OVERALL CASE CANCER SCORE: 0.4%

Local Region Score: 0.2%
Classification: Negative
Regressed Values: X1
(Other)
Overall Cancer Score 0.42%

Local Region Score: 0.3%
Classification: Negative
Regressed Values: X2
(Other)
Overall Cancer Score 0.43%

SYSTEM, USER INTERFACE AND METHOD FOR INTERACTIVE NEGATIVE EXPLANATION OF MACHINE-LEARNING LOCALIZATION MODELS IN HEALTH CARE APPLICATIONS

BACKGROUND

This disclosure relates to a system, user interface, and method for interactive assessing of negative predictions generated by machine learning localization models. The teachings of this disclosure have applications in various fields, including in machine learning health care applications, such as examination of microscope slides, diagnosis of breast cancer in mammograms, or other types of cancer in other radiology modalities (e.g., X-ray, CT, MRI), photographic images (dermatology) and still others. The teachings also have applications in other areas, such as metallurgy, parts inspection, semiconductor manufacturing, and others, where a machine learning localization model is making a prediction based on an input image data set, the prediction is negative, and the user seeks to query the model further.

The use of machine learning models for several health care applications is described in the patent and technical literature. In one example, such models are developed to assist a pathologist in identifying the presence of disease in a 2D or 3D volumetric image of the patent or specimen derived from the patient. For example, the pathologist may be trying to determine if tumor cells (i.e., cancer) are present in a magnified digital image of tissue, such as for example lymph node tissue, breast or prostate cancer tissue obtained from a biopsy. As another example, a machine learning model may assist a radiologist in detecting cancerous cells in a mammogram or chest X-ray. The machine learning models are trained to recognize cancerous cells or tissue from a set of training data (image sets), typically using convolutional neural networks or other classification procedures which are known in the art.

Various techniques and tools are known which address the problem of "model explanation." Model explanation is a process of justifying, in a human-readable manner, why a machine-learning model made a certain recommendation (e.g. diagnosed a patient with cancer). Deep-learning model predictions are notoriously difficult to explain. This is tolerable in use cases such as YouTube video rankings, but completely unacceptable for use cases in high impact applications such as medicine. Pathologists, and other medical professionals, prefer to know not only what the model prediction is, but also why it is so, in order to have confidence in the prediction.

Researchers for the present assignee have developed some basic methods for explaining a model prediction. For example, if a sample or image is diagnosed as "positive" (e.g. has cancer, or high likelihood of cancer), the following methods have been used: (1) a bounding box around a suspected lesion as produced by a detection model and later classified by a classification model is presented to the user, example shown in FIG. 1A; (2) "heat maps", typically with color coding to show degree of confidence of likelihood of particular regions or pixels being cancerous, are presented, example shown in FIG. 1B, see https://ai.googleblog.com/2017/03/assisting-pathologists-in-detecting.html and (3) attention masks are presented to the user, an example of which is shown in FIG. 10.

Despite these advances, options for explaining the lack of a finding (e.g. no cancer) are limited, as it is hard to prove a negative. With most computer-aided detection systems, a medical professional/pathologist/radiologist who believes that a certain region of interest is suspicious of a disease has no way of knowing whether the model producing a negative prediction missed that region or whether the model examined the region and classified it as normal/benign. Due to limited computational resources, in some implementations of machine learning in this domain, a detection model is used initially to find suspected cancerous tissue and only those regions found by the detection model are subsequently classified with a classification model. Accordingly, there is some risk that the detection model may have missed an areas that is potentially cancerous and that therefore the overall resulting prediction of "negative" may not be correct.

This problem of model explanation, in the context of a "negative" prediction, has led many Computer Aided Detection/Diagnosis (CAD) systems existing on the market to fail to deliver improved results. For example, mammography CAD systems have been shown to decrease specificity, partly because such systems employ user interfaces that, while they alert the radiologist with a multitude of findings, they fail to assure the radiologist that findings which the radiologist identified themselves as suspicious were deemed benign by the machine learning model. This disclosure addresses this unmet need.

SUMMARY

In one aspect, a method is disclosed for assessing machine learning model providing a prediction as to the disease state of a patient from 2D or 3D imagery, e.g., an X-ray, CT scan, pathology specimen, of the patient or a sample obtained therefrom. The machine learning model is trained to make a prediction from the 2D or 3D imagery, e.g., cancerous, benign, calcification, lesion, etc. The method includes steps of: a) presenting an image with a risk score or classification associated with the prediction, wherein the image is further augmented with highlighting to indicate one or more regions in the image which affected the prediction produced by the machine learning model; b) providing a user interface tool for highlighting one or more regions of the image, c) receiving a user input highlighting one or more regions of the image; d) subjecting the highlighted one or more regions to inference by the machine learning model; and e) presenting the results of the inference on the one or more regions to the user via the display.

In another aspect, a workstation is described which is configured to assess a machine learning model providing a prediction of a patient from 2D or 3D imagery. The workstation includes a) display for displaying the image of the patient or a sample obtained therefrom along with a risk score or classification associated with the prediction, wherein the image is further augmented with highlighting to indicate one or more regions in the image which affected the prediction produced by the machine learning model; and b) a user interface tool by which the user may highlight on the display one or more regions of the image which the user deems to be suspicious for the disease state, wherein the user invokes the tools to thereby highlight the one or more regions. The display is further configured to present the results of inference performed by the machine learning model on the one or more regions highlighted by the user.

DETAILED DESCRIPTION

In one aspect, a method is disclosed for assessing, i.e., facilitating human understanding, of a machine learning model providing a prediction as to the disease state of a patient from a 2D or 3D image of the patient or a sample obtained therefrom. An example of a 2D image would be a radiology image, such as chest X-ray, or mammogram, or magnified digital image of a pathology specimen. A 3D volumetric image could take the form of a CT scan, nuclear magnetic resonance, or other. In one aspect, this disclosure relates to model interpretability in the situation when the machine learning model produces a negative prediction of the disease state from the image, for example a prediction of "benign" or "low confidence" in the presence of cancer cells in the 2D or 3D image. The threshold at which the prediction is deemed "negative" is not particularly important and can vary depending on such matters as the model sensitivity or user preferences. In the following discussion, the numerical values of cancer score or local region scores are hypothetical and offered only by way of example to illustrate the core ideas of this disclosure and may or may not reflect actual scoring regimes of a given patient sample and machine learning model.

Figure 1A:
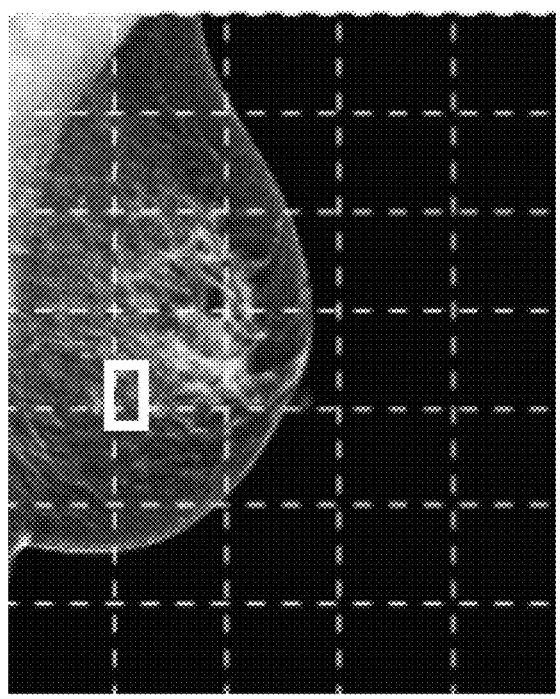
FIG. 1A is a mammogram with a bounding box around a suspected lesion as produced by a detection model and later classified by a classification model.
Figure 1B:
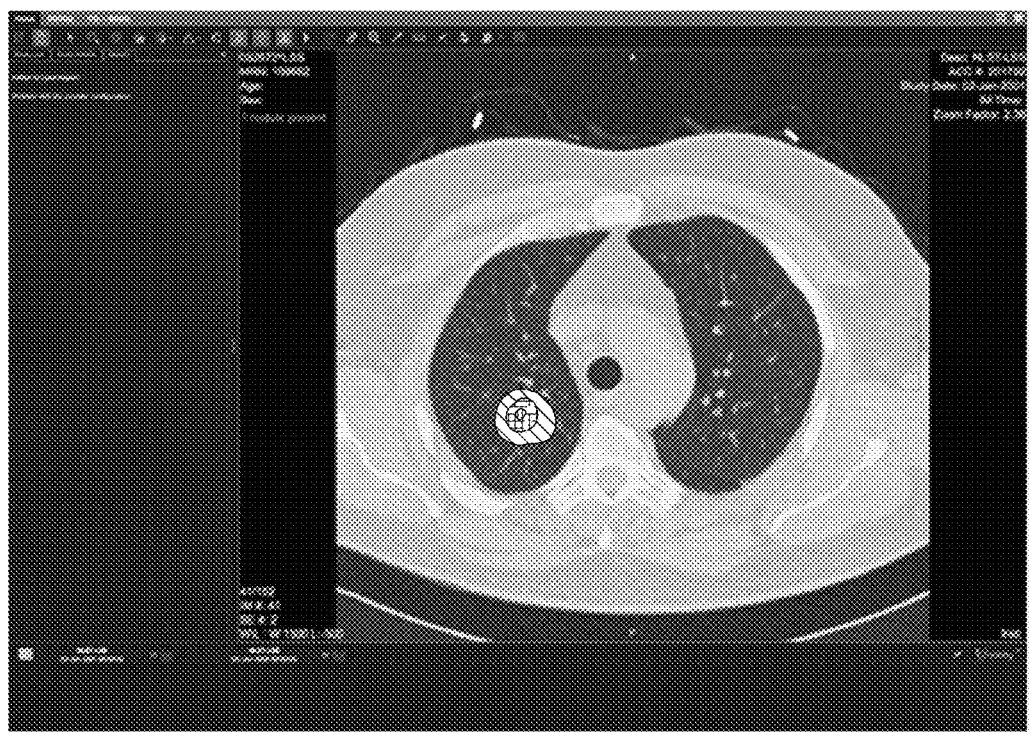
FIG. 1B is CT scan with hatching corresponding to colored areas forming a "heat map" indicating areas of high likelihood of cancer.
Figure 1C:
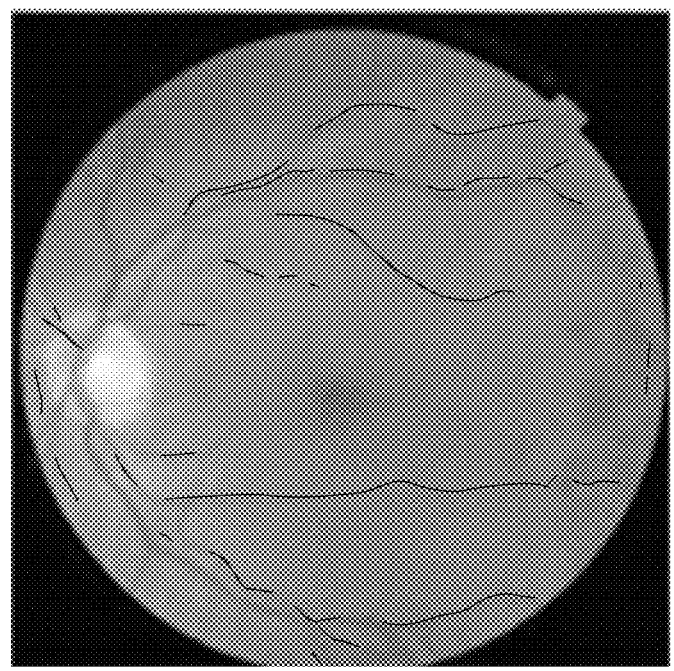
FIG. 1C is retinal photograph with an attention mask (area highlighted with solid lines) indicating those portions of the retinal photograph which contributed to model prediction of a particular eye disease.
Figure 2:
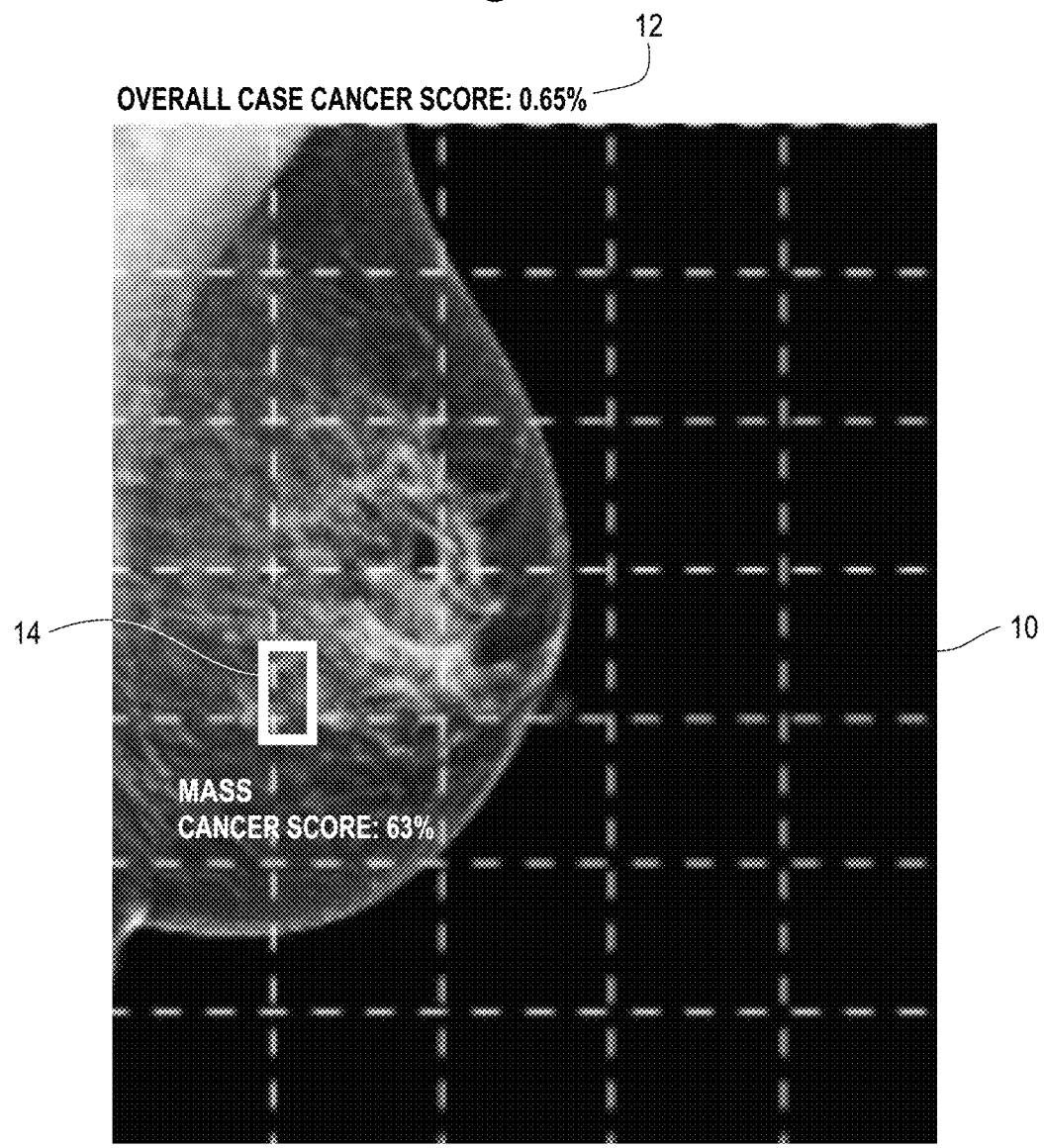
FIG. 2 is a mammogram containing both a risk score (cancer score, =0.6%, likely benign, in this example) along with an overlay in the form of a rectangle identifying a region that affected the machine learning model's diagnostic prediction.

The method includes a first step of presenting on a display of a workstation an image of the patient or a sample obtained therefrom (e.g., mammogram, or magnified tissue image) along with a risk score or classification associated with the prediction. The image is further augmented with highlighting to indicate one or more regions in the image which affected the prediction produced by the machine learning model, such as cluster of cells. An example of this is offered by way of illustration and not limitation in FIG. 2, which is a mammogram 10 of a patient containing both a risk score 12 (cancer score, =0.6%, likely benign, in this example) along with an overlay in the form of a rectangle 14 identifying regions that affected the machine learning model's diagnostic prediction. In this particular example, a machine learning model includes a detection model which is trained to detect likely cancer candidates and the bounding box or rectangle 14 surrounds a candidate. The machine learning model performed inference on the cluster or cells detected by the detection model and they scored "low" and unlikely be cancerous, therefore the overall assessment for the sample is "negative", indicated by the score of 0.65 percent in this example.

Figure 3:
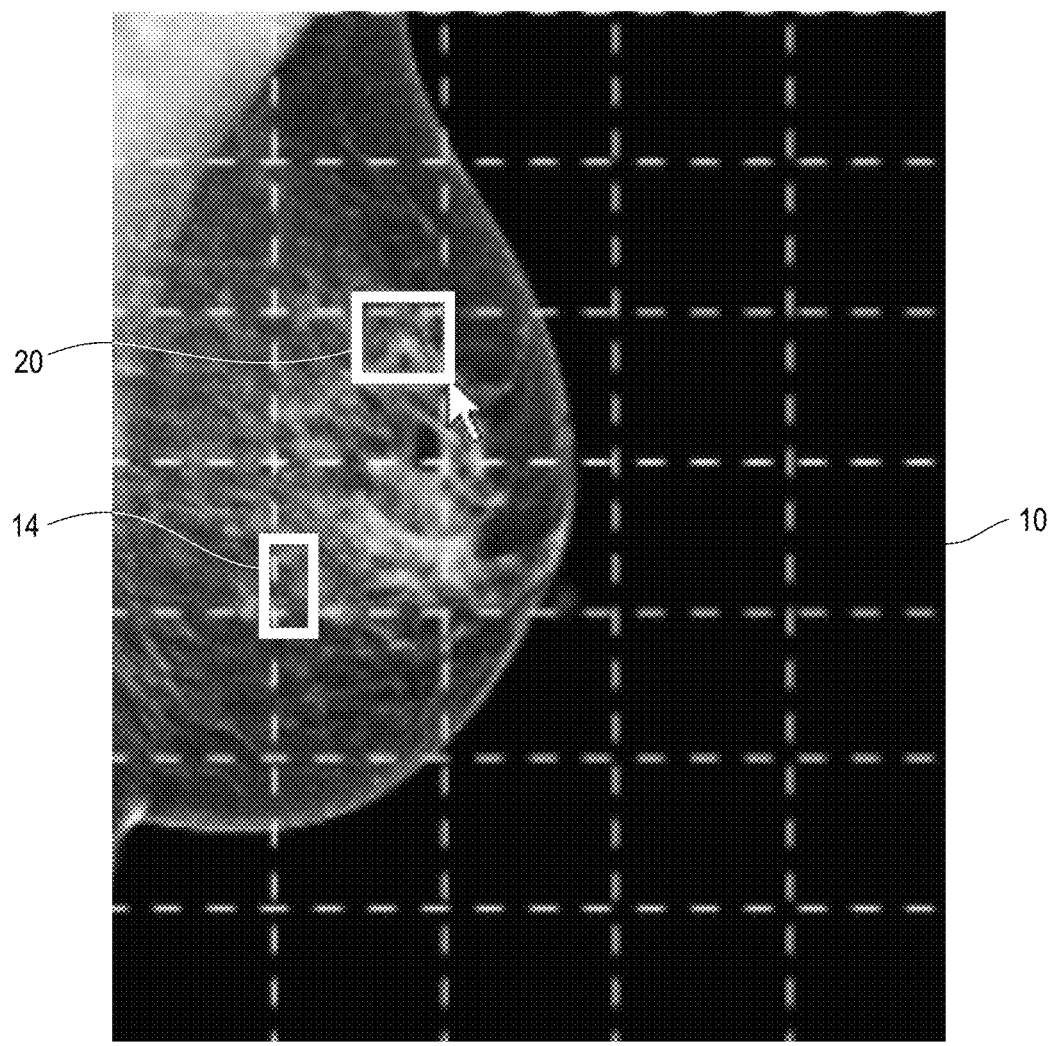
FIG. 3 is an illustration of the mammogram of FIG. 2 but with the user having drawn on the mammogram a new region which the user finds suspicious and requests additional findings. The region could be drawn with the aid of a cursor, or finger or a pen if the mammogram is presented on a touch-sensitive display; the manner in which the region is identified is not particularly important.

The method includes a step of providing a user interface tool by which the user may highlight one or more regions of the image, e.g., which the user deems to be suspicious for the disease state or wishes to query the machine learning model, and receiving an input highlighting the one or more regions. The tool could consist simply of a mouse associated with the display. Alternatively, the display is touch sensitive and the tools take the form of known graphics processing software which records positions on the display which are touched by the user (directly or indirectly, e.g., with a pen) and translates such positions to locations within the image. The manner in which the user highlights the one or more regions is not particularly important and can vary. An example of this step is shown in FIG. 3, which is an illustration of the mammogram of FIG. 2 but with the user having drawn on the mammogram a region 20 with the mouse which the user finds suspicious and requests additional findings. The region could be drawn with the aid of a cursor, or finger if the mammogram is presented on a touch-sensitive display; the manner in which the region is identified is not particularly important. One possible method for drawing a bounding box around the area of interest is described in U.S. Pat. No. 10,013,781 to Christopher Gammage et al., assigned to the assignee of this invention.

The method continues with a step of subjecting the highlighted one or more regions (20 in FIG. 3) to inference by the machine learning model. In this step, the machine learning model processes the pixel data in the region highlighted by the user and generates an output, typically a classification result, or prediction, or score, depending on how the model is configured. In this example, the machine learning model may take the form of a convolutional neural network which is trained from thousands of healthy and cancerous mammograms in order to correctly classify or score new (previously unseen) examples. Deep convolutional neural network pattern recognizers, of the type described here, are widely known in the art of pattern recognition and machine vision, and therefore a detailed description thereof is omitted for the sake of brevity. The Inception-v3 deep convolutional neural network architecture, which is one possible implementation, is described in the scientific literature. See the following references, the content of which is incorporated by reference herein: C. Szegedy et al., *Going Deeper with Convolutions*, arXiv:1409.4842 [cs.CV] (September 2014); C. Szegedy et al., *Rethinking the Inception Architecture for Computer Vision*, arXiv:1512.00567 [cs.CV] (December 2015); see also US patent application of C. Szegedy et al., "Processing Images Using Deep Neural Networks", Ser. No. 14/839,452 filed Aug. 28, 2015. A fourth generation, known as Inception-v4 is considered an alternative architecture. See C. Szegedy et al., *Inception-v4, Inception-ResNet and the Impact of Residual Connections on Learning*, arXiv:1602.0761 [cs.CV] (February 2016). See also US patent application of C. Vanhoucke, "Image Classification Neural Networks", Ser. No. 15/395,530 filed Dec. 30, 2016. The description of the convolutional neural networks in these papers and patent applications is incorporated by reference herein. The use of "attention" models, and related techniques, such as integrated gradients, is described in the scientific and patent literature. D. Bandanau et al., Neural Machine Translation by Jointly Learning to Align and Translate, January 2014 (arXiv:1409.0473[cs.CL]. Choi et al., GRAM: Graph-based attention model for Healthcare Representation Learning, arXiv:1611.07012v3 [cs.LG] April 2017; Choi et al., *RETAIN: an Interpretable Predictive Model for Healthcare using Reverse Time Attention Mechanism*, arXiv:1608.05745v3[cs.GL] February 2017. M. Sundararajan et al., *Axiomatic Attribution for Deep Networks*, arXiv:1703.01365 [cs.LG] (June 2017). Several papers are directed to lung module detection and diagnosis from CT scans using deep learning, including Xiaojie Huang, et al., *Lung Nodule Detection in CT Using* 3D *Convolutional Neural Networks*, The 2017 IEEE International Symposium on Biomedical Imaging, April 2017; Francesco Ciompi et al., *Towards automatic pulmonary nodule management in lung cancer screening with deep learning*, Scientific Reports 7, article no. 46479 Apr. 17, 2017; Wenqing Sun et al., *Computer Aided lung cancer diagnosis with deep learning*, Medical Imaging 2016, Proc. of SPIE vol. 9785 (March 2016); Albert Chon et al., *Deep Convolutional Neural Networks for Lung Cancer Detection*, Stanford University Reports (2017), www.cs231n.stanford.edu/reports/2017/pdfs/518.pdf, and Wafaa Alakwaa, et al., *Lung Cancer Detection and Classification with* 3D *Convolutional Neural Network* (3D-*CNN*), International Journal of Advanced Computer Science and Applications, vol. 8 no. 8. pp 409-417 (2017).

Figure 4:
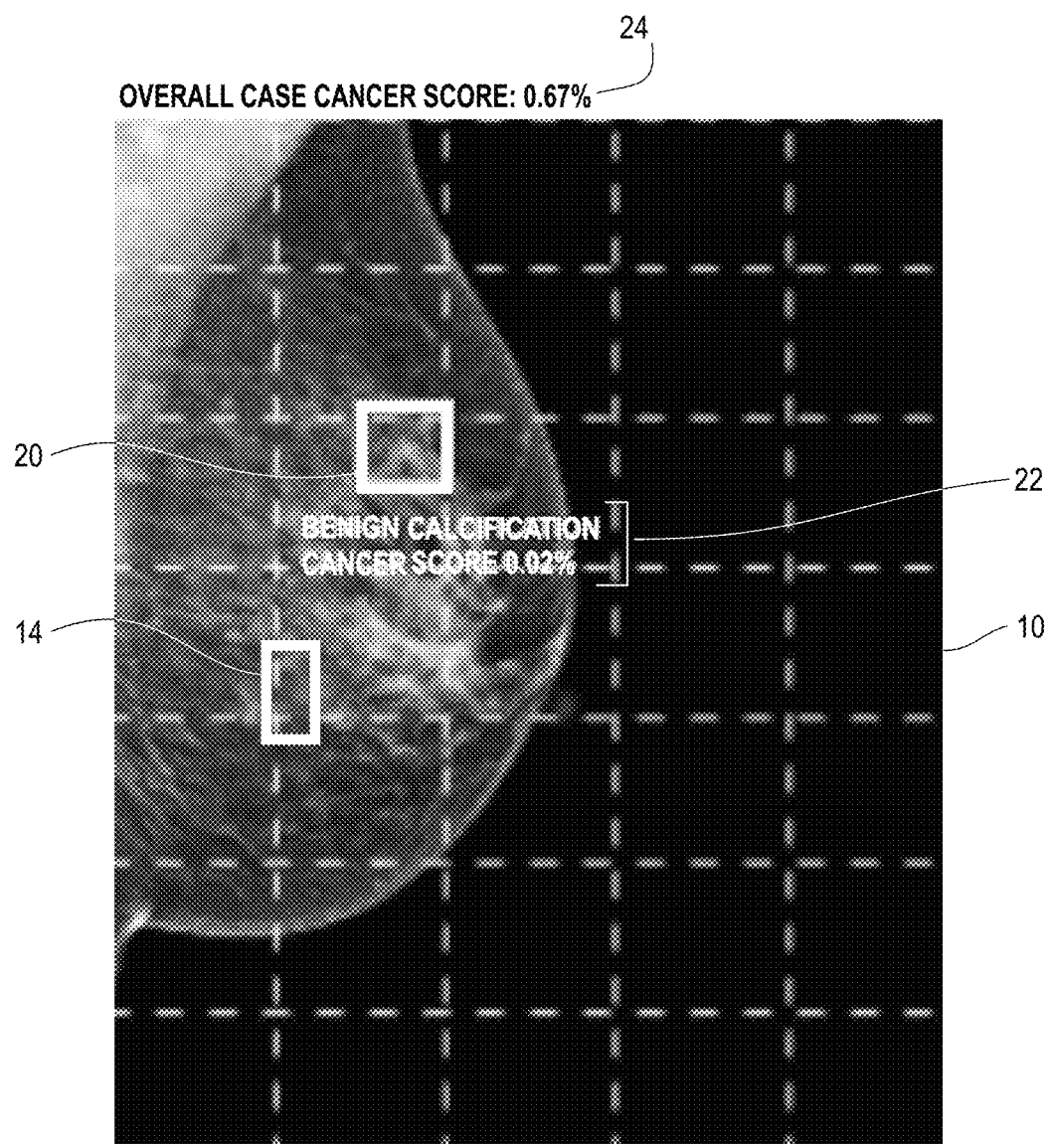
FIG. 4 is an illustration of the mammogram of FIG. 3, after the machine learning model has performed inference on the region highlighted by the user in FIG. 3. The display shows the classification for the user-identified region along with a local region risk score, in this case cancer score of 0.02%. The results of inference may include local region score, classification characteristics, regressed values and other features useful in the interpretation of the region. Such results are presented to the user along with optionally an updated risk score for the overall case. The process the user identifying and highlighting new regions as per FIG. 3, performing inference and presenting results as per FIG. 4 can continue as needed by the user.

The method continues with a step of presenting the results of the inference on the one or more regions (20 in FIG. 3) to the user via the display. An example of this is shown in FIG. 4, which is an illustration of the mammogram of FIG. 3, after the machine learning model has performed inference on the region 20 highlighted by the user in FIG. 3. The display shows the results of the inference at 22 as taking the form of a classification for the user-identified region 20 ("benign calcification") along with a local region risk score, in this case cancer score of 0.02%. The results of inference that may include local region score, classification characteristics, regression values and/or other features useful in the interpretation of the region 20, which are presented to the user. Optionally, the results 22 are presented along with an updated risk score for the overall case, shown at 24. In this particular instance, the overall case risk score increased from 0.65% to 0.67%.

Note: in this example, case level probability increases with every non-zero risk lesion found and decreases with every area examined (we can apply a lower penalty for known unknowns). Which of these effects is stronger depends on how large an area was examined and how serious a lesion was discovered. An alternative numerical example for FIGS. 3 and 4 would be as follows model found one lesion, cancer score 0.6%, overall case score 1.1% (to allow for uncertainty in regions that were not closely examined)

an operator is concerned about another lesion, highlights it, and asks the model to perform inference on it model classifies that lesion as benign with cancer score of 0.2% and increases the case cancer score to 1.2% since that region was not considered earlier, but the case continues to be considered benign. Note that the increase in case score needs to be diminishing with the amount of regions examined in order to be intuitive, as otherwise having a lot of regions examined would lead every case to eventually become "positive."

The process the user identifying new regions as per FIG. 3, performing inference and presenting results as per FIG. 4 can continue as needed by the user.

Figure 5A:
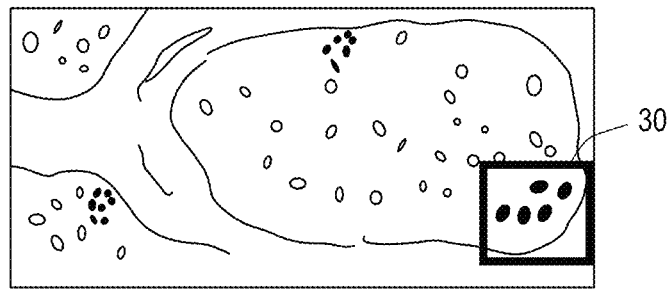
FIG. 5A is an illustration of a tissue image containing both a risk score along with an overlay in the form of a rectangle identifying a cluster of cells that affected the machine learning model's diagnostic prediction.

As noted earlier, the methods of this disclosure are suitable for use with tissue pathology samples, for example image data in the form of magnified digital images of prostate tissue. The methodology will be explained in this context in conjunction with FIGS. 5A-5C. In particular, FIG. 5A is an illustration of a magnified tissue image containing both a risk score (cancer score, =0.40%, benign, in this example) along with an overlay in the form of a rectangle 30 identifying a cluster of cells that affected the machine learning model's diagnostic prediction. In this example, the overall specimen was predicted by the machine learning model to be benign, with a risk score of 0.40%. This risk score and the bounding box 30 are presented to the user on the display of a workstation as shown.

Figure 5B:
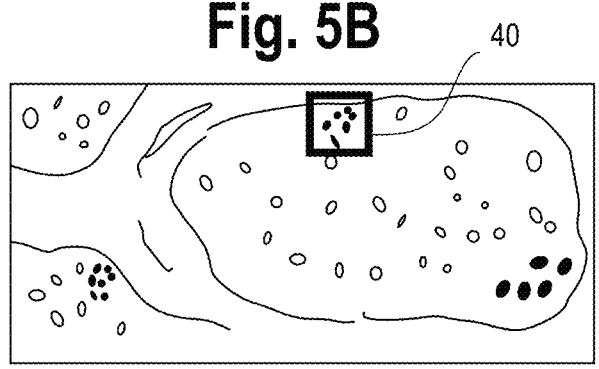
FIG. 5B is an illustration of the tissue image of FIG. 5A but with the user having drawn on the tissue image a new region which the user deems suspicious and requests additional findings. The results of the inference performed on the region drawn by the user are presented on the display.

The pathologist viewing the magnified digital image of the slide on the display of a pathology workstation determines that there are other areas of potential interest in the slide which are not within the bounding box 30, and therefore may wish to know if such other areas are potentially cancerous. Therefore, as shown in FIG. 5B, the user has drawn on the tissue image with user interface tool (e.g., a mouse and graphics processing software) a new region 40 which the user deems suspicious and requests additional findings from the machine learning model. The pixel data associated with the region 40 are provided as input to the machine learning model. The results of the inference performed on the region 40 drawn by the user are presented on the display, as indicated at 42. These results include a local region score (0.20%), a classification result (negative) and optionally regression values or other information. An updated overall cancer score for the sample is generated and displayed, in this example 0.42%. In this example, the classification of the additional cluster of cells within the box 40 has caused the overall cancer score to increase from 0.40 percent to 0.42 percent.

Figure 5C:
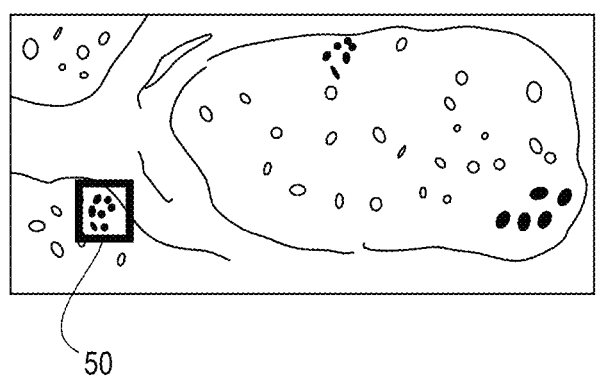
FIG. 5C is an illustration of the tissue image of FIG. 5A with the user having drawn on the image another new region which was deemed suspicious. The results of the inference performed on the new region are presented on the display.

In this example, the user has elected to highlight still another area of the tissue specimen for further scoring/inference by the machine learning model. In this example, as shown in FIG. 5C, the user has drawn on the image another new region 50 which was deemed suspicious. The results of the inference performed on the new region are presented on the display as indicated at 52.

Note that in this example, there may be intermediate steps such as zooming and panning to new locations within a given tissue image but the process described above in FIGS. 5A-5C is essentially unchanged. The user selection of new areas as indicated in FIG. 5C can of course continue until the user is satisfied with the negative model prediction for the tissue specimen.

Figure 6:
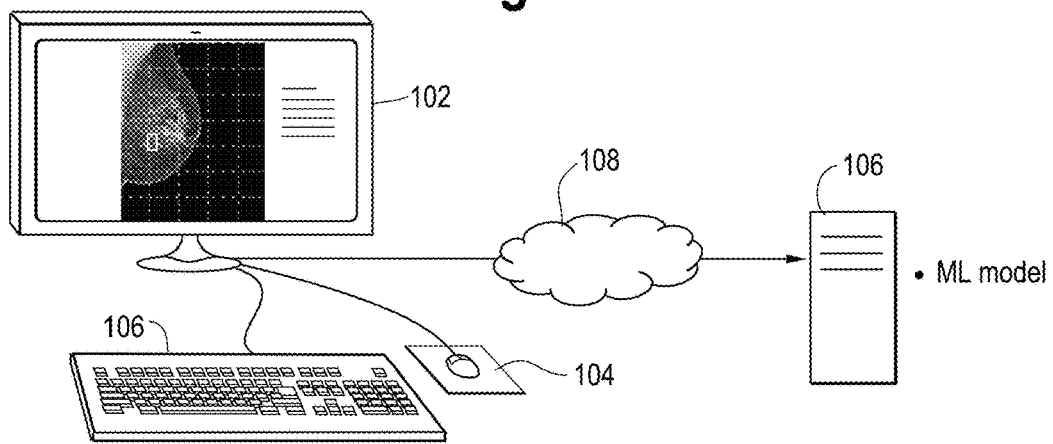
FIG. 6 is an illustration of one example of a computing environment in which the methods of this disclosure can be practiced.

Referring now to FIG. 6, the method of this disclosure can be implemented in a workstation 100 which is configured to facilitate human understanding of a machine learning model providing a prediction as to the disease state of a patient from a 2D or 3D image of the patient or a sample obtained therefrom. The machine learning model produces a negative prediction of the disease state from the image, e.g., by way of a classification result or score which is presented to the user. The workstation includes a) display 102 for displaying the image of the patient or a sample obtained therefrom along with a risk score or classification associated with the prediction. The image is further augmented with highlighting to indicate one or more regions in the image which affected the negative prediction produced by the machine learning model (see FIGS. 3 and 5B). The workstation includes a user interface tool, e.g., mouse 104, or touch sensitive display, by which the user may highlight on the display one or more regions of the image which the user deems to be suspicious for disease. The user invokes the tools, e.g., mouse, to thereby highlight the one or more regions. The display is further configured to present the results of inference performed by the machine learning model on the one or more regions highlighted by the user, as explained previously. Once the user has highlighted the area of interest, e.g., using the mouse 104, the user can invoke the machine learning model by entering a command via a suitable menu on the display, such as by clicking an "apply model" icon on the display or by using the keyboard 106 to enter an appropriate command.

The machine learning model 110 can be resident in the workstation 100, or more typically it can be implemented by computing resource 106 on a computer network 108. In one possible configuration, there are several machine learning models available. In the tissue pathology situation, the user may view the specimen at a higher magnification, e.g., 40×, and designate a new region at that magnification (e.g., region 40 in FIG. 5B) and invoke a particular machine learning model trained to identify cancer cells at that magnification, whereas they may also view the specimen and highlight a region of cells at low magnification, e.g., 10X, e.g., the region 50 of FIG. 5C, and a low magnification (10×) machine learning model is used for that inference task.

Figure 7:
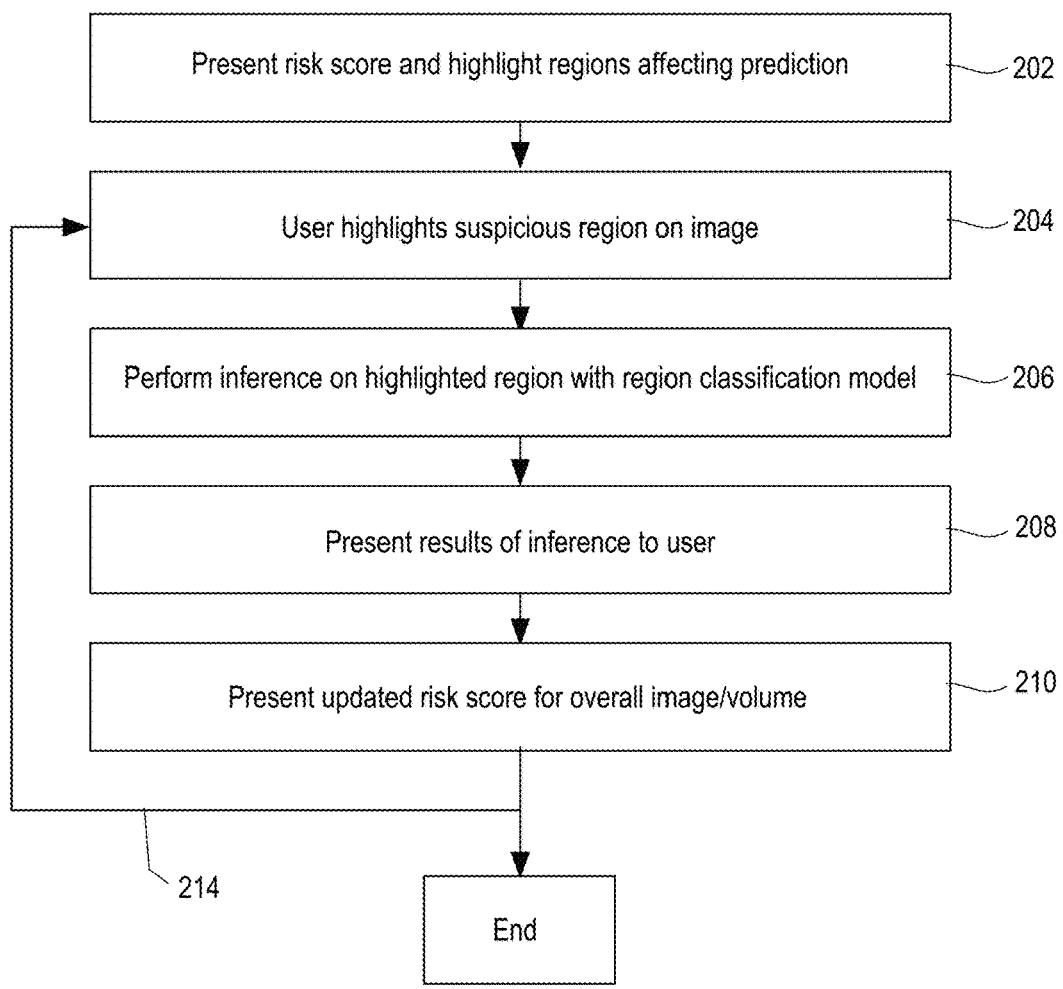
FIG. 7 is a flow chart showing one embodiment of the processing performed in the computing environment of FIG. 6 to perform the method.

FIG. 7 is a flow chart showing one embodiment of the processing performed in the computing environment of FIG. 6 to perform the method. A machine learning model performs inference on a 2D or 3D image data set of a patient or sample obtained therefrom. The model provides a prediction as to the disease state of a patient, and in one example a negative prediction of the disease state. The methodology indicated at 200 includes the following steps:

Step 202: present on a display of a workstation the image of the patient or a sample obtained therefrom along with a risk score or classification associated with the prediction. The image is further augmented with highlighting to indicate one or more regions in the image which affected the prediction produced by the machine learning model.

Step 204: provide a tool by which the user may highlight one or more regions of the image which the user deems to be suspicious for the disease state. The user invokes the tools to thereby highlight the one or more regions, and such input is received by the workstation.

Step 206: perform inference on the highlighted one or more regions with the machine learning model.

Step 208: present the results of the inference on the one or more regions to the user via the display.

Optional step 210: present an updated risk score for the overall 2D image/3D volume.

The process can loop back as indicated at step 214 and steps 204, 206 and 208, and 210 can repeat; this loop applies to the situation where the user specifies additional regions, as explained in FIGS. 5A-5C.

As will be apparent from FIGS. 2-6, it will be apparent that an interface for a workstation has been described, which is configured to facilitate human understanding of a machine learning model providing a prediction as to the disease state of a patient from a 2D or 3D image of the patient or a sample obtained therefrom. The machine learning model produces a prediction of the disease state from the image, e.g., a negative prediction such as "benign." The interface includes a display (102, FIG. 6) for displaying the image of the patient or a sample obtained therefrom along with a risk score or classification associated with the prediction. The image is further augmented with highlighting to indicate one or more regions in the image which affected the prediction produced by the machine learning model. The interface includes a tool (e.g., mouse 104) by which the user may highlight on the display one or more regions of the image, e.g., regions which the user deems to be suspicious for the disease state, wherein the user invokes the tools to thereby highlight the one or more regions, as explained in conjunction with FIGS. 3, 4 and 5A-5C.

Further Considerations

The method could be used to further examine an image even after the machine learning model has are already classified the specimen as a positive. An operator may suspect that there is another lesion worth reporting (either more or less severe) and would want the model to explicitly examine it. Therefore, the method proceeds with the steps of highlighting the additional region, initiating model inference, and then generating the results of the inference and presenting it on the workstation display.

The above description focuses on classification+localization problems, but the same method could be used in other ways, for example in segmentation and regression problems.

A. Segmentation

For example, an ultrasound image is presented on the workstation and the machine learning model is used to identify a prostate on the ultrasound image. An operator viewing the image sees a segmentation mask outline surrounding the prostate, and may suspect that some tissue that was not marked within the mask also belonged to the prostate. The user highlights this additional area and initiates model inference with keyboard or mouse action. The model then either explains that this region is actually urethra, for example, or the model "agrees" to add that region to the segmentation mask.

B. Regression Problems

For example, a machine learning model may be configured to answer a regression problem, such as "What is the bone age of a patient imaged with an x-ray?" An X-ray of a bone along with the prediction of the model is presented on the workstation display. The operator suspects that a certain region indicates a higher age, highlights it, initiates inference, and the model updates its prediction accordingly. This general procedure can of course be applied to other types of regression problems; the bone age example is offered by way of illustration and not limitation.

The teachings also have applications in other areas, such as metallurgy, parts inspection, semiconductor manufacturing, and others, where a machine learning localization model is making a prediction regarding an object based on an input image data set. For example, the prediction is negative (e.g., no defect is present, or no undesirable impurity is present in a metallurgical sample), and the user seeks to query the model further. The method follows the same basic approaches as described above:

a) present on a display of a workstation the image of the object along with a score or classification associated with the prediction. The image is further augmented with highlighting to indicate one or more regions in the image which affected the prediction produced by the machine learning model;

b) provide a tool by which the user may highlight one or more additional regions of the image which the user deems to be of further interest relative to the prediction (such as for example, potential defects, impurities, etc.), wherein the user invokes the tools to thereby highlight the one or more regions;

c) subject the highlighted one or more regions to inference by the machine learning model; and d) present the results of the inference on the one or more regions to the user via the display.

The appended claims are offered by way of further description of the disclosed methods, workstation and user interface.

I claim:

1. A method for assessing a machine learning model providing a prediction as to the disease state of a patient from a 2D or 3D image, comprising the steps of:
   a) presenting an image with a risk score or classification associated with the prediction, wherein the image is further augmented with highlighting to indicate one or more regions in the image which affected the prediction produced by the machine learning model;
   b) providing a user interface tool for highlighting one or more different regions of the image,
   c) receiving a user input highlighting one or more different regions of the image;
   d) subjecting the highlighted one or more different regions to inference by the machine learning model; and
   e) presenting the results of the inference on the one or more different regions to the user via the display.

2. The method of claim 1, further comprising the steps of receiving user input highlighting still further different regions of the image and performing steps d) and e) for such still further different regions.

3. The method of claim 1, wherein the prediction is associated with a risk score, and wherein step e) comprises the step of generating a new risk score.

4. The method of claim 1, wherein the machine learning model comprises a convolutional neural network trained to recognize the presence of cancer cells in the image.

5. The method of claim 1, wherein the image comprises a magnified digital image of a tissue specimen.

6. The method of claim 1, wherein the image comprises a 2D radiological image.

7. The method of claim 6, wherein the image is selected from the group of images consisting of a mammogram and a chest X-ray.

8. The method of claim 1, wherein the image comprises a 3D radiological image obtained from either nuclear magnetic resonance (NMR) or computed tomography (CT).

9. The method of claim 1, wherein the tool comprises a mouse associated with the display.

10. The method of claim 1, wherein the display is touch sensitive and wherein the tool comprises graphics processing which record positions on the display which are touched directly or indirectly by the user and translate such positions to locations within the image.

11. A workstation configured to assess a machine learning model providing a prediction as to the disease state of a patient from a 2D or 3D image of the patient or a sample obtained therefrom, wherein the machine learning model produces a prediction of the disease state from the image, wherein the workstation comprises:
   a) display for displaying the image of the patient or a sample obtained therefrom along with a risk score or classification associated with the prediction, wherein the image is further augmented with highlighting to indicate one or more regions in the image which affected the prediction produced by the machine learning model;
   b) a user interface tool by which the user may highlight on the display one or more different regions of the image, wherein the user invokes the tool to thereby highlight the one or more different regions;
   wherein the display is further configured to present the results of inference performed by the machine learning model on the one or more different regions highlighted by the user.

12. The workstation of claim 11, wherein the workstation further comprises a processing unit in communication with the display and wherein the machine learning model is implemented in the processing unit.

13. The workstation of claim 11, wherein the machine learning model comprises a convolutional neural network trained to recognize the presence of cancer in the image.

14. The workstation of claim 11, wherein the image comprises a magnified digital image of a tissue specimen.

15. The workstation of claim 11, wherein the image comprises a 2D radiological image.

16. The workstation of claim 15, wherein the image is selected from the group of images consisting of a mammogram and a chest X-ray.

17. The workstation of claim 11, wherein the image comprises a 3D radiological image obtained from either nuclear magnetic resonance or computed tomography.

18. The workstation of claim 11, wherein the tool comprises a mouse associated with the display.

19. The workstation of claim 11, wherein the display is touch sensitive and wherein the tool comprises graphics processing which record positions on the display which are touched directly or indirectly by the user and translate such positions to locations within the image.

20. An interface for a workstation configured to assess a machine learning model providing a prediction as to the disease state of a patient from a 2D or 3D image of the patient or a sample obtained therefrom, wherein the machine learning model produces a prediction of the disease state from the image, wherein the interface comprises:
   a display for displaying the image of the patient or a sample obtained therefrom along with a risk score or classification associated with the prediction, wherein the image is further augmented with highlighting to indicate one or more regions in the image which affected the prediction produced by the machine learning model; and
   a user interface tool by which the user may highlight on the display one or more different regions of the image which the user deems to be suspicious for the disease state, wherein the user invokes the tools to thereby highlight the one or more different regions.

* * * * *